United States Patent [19]
Pogo et al.

[11] Patent Number: 5,911,991
[45] Date of Patent: *Jun. 15, 1999

[54] MALARIAL BINDING SITE IN DUFFY BLOOD GROUP PROTEIN

[75] Inventors: A. Oscar Pogo, Pelham Heights; Asok Chaudhuri, Hicksville, both of N.Y.

[73] Assignee: New York Blood Center, Inc., New York, N.Y.

[ * ] Notice: This patent is subject to a terminal disclaimer.

[21] Appl. No.: 08/749,526

[22] Filed: Nov. 15, 1996

Related U.S. Application Data

[63] Continuation-in-part of application No. 08/140,797, Oct. 21, 1993, Pat. No. 5,578,714.

[51] Int. Cl.$^6$ .......................... A61K 38/00; C07K 14/705
[52] U.S. Cl. ..................................... 424/185.1; 424/268.1; 530/380; 530/395
[58] Field of Search ..................................... 530/300, 350, 530/395, 380; 424/185.1, 268.1, 272.1, 193.1

[56] References Cited

U.S. PATENT DOCUMENTS

| | | |
|---|---|---|
| 5,101,017 | 3/1992 | Rubinstein et al. . |
| 5,198,347 | 3/1993 | Miller et al. . |
| 5,541,292 | 7/1996 | Miller et al. . |
| 5,578,714 | 11/1996 | Pogo et al. .............................. 536/23.5 |
| 5,614,194 | 3/1997 | Colman et al. . |

OTHER PUBLICATIONS

Goodman, et al., Methods in Enzymology 68:75–90, 1979.
Broome et al., Biochemistry 75(6):2746–49, 1978.
Nichols, et al., J. Exp. Med. 166:776–785, 1987.
Asok Chaudhuri, Valerie Zbrzezna, Carol Johnson, Margaret Nichols, Pablo Rubenstein, W. Laurence Marsh, and A. Oscar Pogo, "Purification and Characterization of an Erythrocyte Membrane Protein Complex Carrying Duffy Blood Group Antigenicity," (1989) *The Journal of Biological Chemistry* 264, 13770–13774.
Asok Chaudhuri, Julia Polyakova, Valerie Zbrzezna, Kenneth Williams, Subhash Gulati, and A. Oscar Pogo, "Cloning of Glycoprotein D cDNA, Which Encodes the Major Subunit of the Duffy Blood Group System and the Receptor for the Plasmodium Vivax Malaria Parasite," (1993) *Proc. Natl. Acad. Sci. USA* 90, 10793–10797.
S. Mathew, A. Chaudhuri, V.V.V.S Murty and A.O. Pogo, "Confirmation of Duffy Blood Group antigen Locus (FY) at 1q22→q23 by Fluorescence in Situ Hybridization," (1994) *Cytogenet Cell Genet* 67, 68.

Asok Chaudhuri, Valerie Zbrzezna, Julia Polyakova, A. Oscar Pogo, Joseph Hesselgesser, and Richard Horuk, "Expression of the Duffy Antigen in K562 Cells," (1994) *The Journal of Biological Chemistry* 269, 7835–7838.
Asok Chaudhuri and A. Oscar Pogo, "The Duffy Blood Group System and Malaria," (1995) *Blood Cell Biochemistry, Molecular Basis of Major Human Blood Group Antigens* 6, 243–265.
Asok Chaudhuri, Julia Polyakova, Valeri Zbrzezna, and A. Oscar Pogo, "The Coding Sequence of Duffy Blood Group Gene in Humans and Simians: Restriction Fragment Length Polymorphism, Antibody and Malarial Parasite Specificities, and Expression in Nonerythroid Tissues in Duffy–Negative Individuals," (1995) *Blood* 85, 615–621.
A.O. Pogo, A. Chaudhuri, "Duffy and Receptors for P. Vivax and Chemotactic Peptides," (1995) *TCB* 4, 269–276.
Christophe Tournamille, Yves Colin, Jean Pierre Cartron & Caroline Le Van Kim, "Disruption of a GATA Motif in the Duffy Gene Promoter Abolishes Erythroid Gene Expression in Duffy–Negative Individuals," (1995) *Nature Genetics* 10, 224–228.
Sadahiko Iwamoto, Toshinori Omni, Eiji Kajii, and Shigenori Ikemoto, "Genomic Organization of the Glycoprotein D Gene: Duffy Blood Group $Fy^a/Fy^b$ Alloantigen System is Associated with a Polymorphism at the 44–Amino Acid Residue" (1995) *Blood* 85, 622–626.
Sadahiko Iwamoto, Jianping Li, Toshinori Omi, Sigenori Ikemoto, and Eiji Kajii, "Identification of a Novel Exon and Spliced Form of Duffy mRNA That is the Predominant Transcript Both Erythroid and Postcapillary Venule Endothelium" (1996) *Blood* 87, 378–385.

*Primary Examiner*—Thomas M. Cunningham
*Attorney, Agent, or Firm*—Hoffmann & Baron, LLP

[57] ABSTRACT

A composition and method for inhibiting binding of malarial Duffy-binding ligand to Duffy blood group antigens on mammalian erythrocytes is disclosed. The composition includes a Duffy-related peptide which interferes with binding between Duffy antigen expressed on erythrocyte cell surfaces and the Duffy-binding ligands of merozoites. Particularly preferred peptides are the peptides having the sequences AELSPSTENSSQLDFEDVWNSSYGVNDS-FPDGDYD (SEQ ID NO:1) or AELSPSTQNSSQLNSDL-WNFSYDGNDSFPDVDYD (SEQ ID NO:4), as well as peptides which comprise either of those sequences in their primary structure, or other peptides having equivalent function. A method is disclosed which comprises administering a Duffy-based peptide which interferes with malarial binding to Duffy antigen in an amount sufficient to inhibit binding of merozoites to erythrocytes.

16 Claims, 3 Drawing Sheets

FIG-1A

HPEP35  AELSPST E NSSQL DFE D V WN S SY GV NDSFPD G DYD  (SEQ ID NO:1)
                   ↔       ↔↔    ↔    ↔  ↔↔       ↔
RHPEP34 AELSPST Q NSSQL -NS D L WN F SY DG NDSFPD V DYD  (SEQ ID NO:4)

FIG-1B

| | | |
|---|---|---|
| HPEP35 | AELSPSTENSSQLDFEDVWNSSYGVNDSFPDGDYD | (SEQ ID NO:1) |
| HPEP13 | AELSPSTENSSQL | (SEQ ID NO:7) |
| HPEP22 | DFEDVWNSSYGVNDSFPDGDYD | (SEQ ID NO:8) |
| HPEP3850 | PSTENSSQLDFEDVWNSSYGVNDS | (SEQ ID NO:9) |

MALARIAL BINDING SITE IN DUFFY BLOOD GROUP PROTEIN

This application is a continuation-in-part of U.S. patent application Ser. No. 08/140,797, filed on Oct. 21, 1993, now U.S. Pat. No. 5,578,714, the entire disclosure of which is incorporated herein by reference.

This invention was made with Government support under Grant No. HL53297 NHLB1, awarded by the National Institutes of Health. The Government has certain rights in this invention.

BACKGROUND OF THE INVENTION

The invention relates to the Duffy blood group protein (also known as gp-Fy) and its function in malaria. More specifically, the invention relates to peptides having amino acid sequences characteristic of Duffy proteins, compositions containing such peptides, and methods of using such compositions to combat malaria Malaria is the most prevalent infectious disease of mankind. Its widespread geographic distribution together with the severe pathologic consequences of the infection make malaria a major medical and financial burden for many of the developing nations.

There are several different kinds of malaria, one of which is caused by the parasite *Plasmodium vivax*, which attacks the red blood cells of susceptible individuals. A genetic trait of special interest with regard to *P. vivax* is the absence of antigens encoded by the blood group system called Duffy (Livingston 1984). It has been shown that individuals whose red blood cells lack the product of the Duffy genes are not susceptible to the penetration of *P. vivax* owing to the fact that Duffy molecules serve as the receptor for the parasite. (Miller et al. 1976).

Malarial parasites are transmitted from host to host by the feeding females of several species of the genus Anopheles. It is in the mosquito that the sexual phase of the life cycle of *P. vivax* takes place, leading to the production of sporozoites. After their introduction into a "new" host, these sporozoites reside in the parenchymal cells of the liver and multiply asexually causing the eventual rupture of hepatic cells and the release of asexual forms (merozoites) into the blood stream. The circulating merozoites actively penetrate into red blood cells in a nearly synchronous fashion and, because the rate of growth and cell division of *P. vivax* is essentially identical, the infected erythrocytes simultaneously reach the stage of parasite load at which they burst. This produces the typical cycles of fever every 48 hours, a condition known as "tertian" malaria. Immunity to *P. vivax* is commonly only partial in nature, which allows the occurrence of superinfections that evolve independently, causing an overlap in the cycles of parasite release leading to fever cycles of apparently shorter periods.

*P. vivax* infection may persist without treatment for as long as five years. *P. vivax* parasitemias are relatively low-grade, primarily because the parasites favor the few young red blood cells or reticulocytes that exist in peripheral blood.

Invasion of erythrocytes by Plasmodium merozoites is a multi-step process that requires a series of specific molecular interactions between the invading merozoite and the target erythrocyte. *P. vivax* and the related simian malarial parasite, *P. knowlesi*, both require interaction with the erythrocyte chemokine receptor, also known as the Duffy blood group antigen, to invade human erythrocytes (Miller et al. 1975; Miller et al. 1976; Horuk et al. 1993). The Duffy blood group system consists of two principal antigens $Fy^a$ and $Fy^b$ produced by co-dominant alleles, FY*A and FY*B. Antisera anti-$Fy^a$ and anti-$Fy^b$ have been used to define four phenotypes, Fy(a+b−), Fy(a−b+), Fy(a+b+) and Fy(a−b−) (Marsh 1975). Neither of these antisera agglutinates Duffy Fy(a−b−) cells, the predominant phenotype in Africans and African-Americans. Antisera defining the other Duffy phenotypes, Fy3, Fy4 and Fy5, are very rare. A murine monoclonal antibody, anti-Fy6, defines a Duffy antigenic determinant present in all red blood cells except Fy(a−b−) cells (Nichols 1987). Accordingly, erythrocytes reacting with the Duffy antisera or anti-Fy6 are designated "Duffy-positive," while unreactive erythrocytes are designated "Duffy-negative." Duffy-negative human erythrocytes, which lack the Duffy blood group antigen, are completely resistant to invasion by these parasites.

Unlike *P. vivax*, however, *P. knowlesi* can also invade the erythrocytes of rhesus monkeys, which are commonly used as hosts for *P. knowlesi* in the laboratory. Although *P. knowlesi* is absolutely dependent on the Duffy blood group antigen for invasion of human erythrocytes, *P. knowlesi* can use both Duffy antigen-dependent and alternate, independent pathways to invade rhesus erythrocytes (Haynes et al. 1988). The erythrocyte receptors involved in these Duffy antigen-independent invasion pathways of *P. knowlesi* are not known.

In contrast to *P. vivax*, *P. falciparum* can invade both Duffy-positive and -negative human erythrocytes with similar efficiencies. This indicates that *P. falciparum* does not require the Duffy antigen for invasion. Most *P. falciparum* strains studied thus far in the laboratory use sialic acid residues on glycophorins as receptors for optimal invasion of human erythrocytes. However, some *P. falciparum* strains can also use alternate receptors to invade human erythrocytes, although at reduced levels (Mitchell et al. 1986; Hadley et al. 1986; Perkins et al. 1988; Dolan et al. 1994.

The parasite ligands that bind to the several erythrocyte receptors described above belong to a family of erythrocyte binding proteins. This family includes the Duffy-binding proteins of *P. vivax* and *P. knowlesi* (designated "α"); the *P. knowlesi* proteins, designated "β" and "γ," which bind as yet unidentified receptors on rhesus erythrocytes; and the *P. falciparum* protein, designated "EBA-175," which binds sialic acid residues of glycophorin A on human erythrocytes (Adams et al. 1992). The Duffy receptors of *P. vivax* and *P. knowlesi* are described in detail in U.S. Pat. Nos. 5,198,347 and 5,541,292 to Miller et al.

Each protein of this family contains two cysteine-rich domains which contain cysteines as well as a number of aromatic amino acid residues that are conserved in position. The functional binding domain of each erythrocyte binding ligand lies in Region II, the 5' cysteine-rich domain of each protein (Chitnis et al. 1994; Sim et al. 1994). These cysteine-rich domains are referred to as Duffy-binding-like (DBL) domains since the first of these domains to be shown to possess adhesive properties was derived from the *P. vivax* protein that binds the Duffy antigen. DBL domains are also found in the var genes, which encode the variant surface antigens of *P. falciparum*. They define a large family of Plasmodium proteins, the DBL superfamily, which includes both the erythrocyte binding proteins and the variant surface antigens of Plasmodium (Su et al. 1995; Smith et al. 1995; Baruch et al. 1995).

*P. vivax* exhibits considerable antigenic diversity and variation, as do other malarial Plasmodium species (Hommel 1985), although it has been recently shown that antigenic components of *P. vivax* sporozoites exist that are common to parasites from different isolates (Zavala et al. 1985). The merozoites of different strains of *P. vivax* share the same receptor for penetration into red blood cells, i.e., the Duffy molecule (Miller et al. 1976). Recognizing this feature carries implications for the development of vaccines. In addition, regardless of the parasite's capacity to vary other antigenic molecules, its recognition molecule, i.e., the molecule that binds to the Duffy molecule, must remain constant since it is the complementarily between this molecule and the invariant receptor that allows the penetration of merozoites into erythrocytes and, thus, the continuity of the infection. Changes in the ligand specificity of this molecule would result in the loss of the parasite's capacity to infect, since *P. vivax* merozoites appear to be unable to utilize other human red blood cell receptors for their penetration in vivo, as shown by the resistance to infection of Duffy-negative erythrocytes.

In view of the above considerations, it is clear that existing knowledge concerning the malarial binding site on erythrocytes has been insufficient to permit molecular approaches to the treatment and prophylaxis of malaria. Lacking an understanding of the molecular basis for the interaction between the merozoite and the Duffy antigen has been a serious impediment preventing the development of compositions and methods by which that interaction, and the concomitant infection, can be effectively inhibited or eliminated.

Accordingly, it is one of the purposes of this invention to overcome the above limitations in the prevention and treatment of malaria, by providing a composition and method capable of inhibiting or preventing the specific parasite-erythrocyte interaction and subsequent infection. Other purposes will present themselves to the skilled artisan to render the invention useful in particular contexts.

SUMMARY OF THE INVENTION

It has now been discovered that these and other objectives can be achieved by the present invention, which provides a peptide comprising an amino acid sequence characteristic of a Duffy protein and having a specific binding affinity for a malarial Duffy-binding ligand. The peptide can be characteristic of a human or primate Duffy protein. The human Duffy protein can be a gp-Fyα protein or a gp-Fyβ protein. Preferably, the peptide has an amino acid sequence which comprises AELSPSTENSSQLDFEDVWNSSYGVNDSFPDGDYD (SEQ ID NO:1). The peptide can have an amino acid sequence which comprises one of:

(a) MASSGYVLQAELSPSTENSSQLDFEDVWNSSYGVNDSFPDGDYDANLEAAAPCHSCNLLDDSALPF (SEQ ID NO:2);

(b) MGNCLHRAELSPSTENSSQLDFEDVWNSSYGVNDSFPDGDYDANLEAAAPCHSCNLLDDSALPF (SEQ ID NO:3); or (c) a fragment of sequence (a) or sequence (b) containing the sequence AELSPSTENSSQLDFEDVWNSSYGVNDSFPDGDYD (SEQ ID NO:1).

As noted, the peptide of the invention can have an amino acid sequence comprising a malarial-binding domain of a Duffy protein of a non-human primate. Thus, the peptide can have an amino acid sequence which comprises AELSPSTQNSSQLNSDLWNFSYDGNDSFPDVDYD (SEQ ID NO:4), GELSPSTENSSQLNLEDLWDFSYDGND-SLPEIDYD (SEQ ID NO:5), or VELSPSTENSSQLNLEDLWNFSYNGNDSFPEIDYD (SEQ ID NO:6).

Regardless of source, the peptide preferably has an amino acid sequence comprising a domain of a Duffy protein which is specifically bound by the Rubinstein antibody.

Preferably, the malarial Duffy-binding ligand is a malarial Duffy-binding ligand of *Plasmodium vivax* or a malarial Duffy-binding ligand of *Plasmodium knowlesi*.

The invention further comprises a composition useful to protect a warm-blooded animal against malaria infection, comprising an amount effective therefor of a peptide of the invention, i.e., a peptide containing a domain of a Duffy protein having a specific binding affinity for a malarial Duffy-binding ligand, said peptide in admixture with a physiologically acceptable diluent. Preferably, the peptide in the composition is conjugated to a carrier.

The composition, therefore, includes a peptide which inhibits binding of a malaria organism to a red blood cell. Preferably, the malaria organism is *Plasmodium vivax* or *Plasmodium knowlesi*.

The invention further includes a method of protecting a warm-blooded animal from malarial infection, comprising administering to said animal an effective amount therefor of a peptide of the invention, i.e., a peptide comprising a domain of a Duffy protein having specific binding affinity for a malarial Duffy-binding ligand. Thus, the peptide useful according to the invention inhibits binding of a malaria organism to a red blood cell.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings, wherein:

FIG. 1A illustrates the relationships between the human and rhesus malarial-binding domains of the respective Duffy proteins of these species;

FIG. 1B illustrates a malarial-inhibiting peptide of the invention (HPEP35) and its relationships to other related peptides which do not exhibit malarial-binding affinity;

DETAILED DESCRIPTION OF THE PREFERRED EMBODIMENTS

Figure 2:
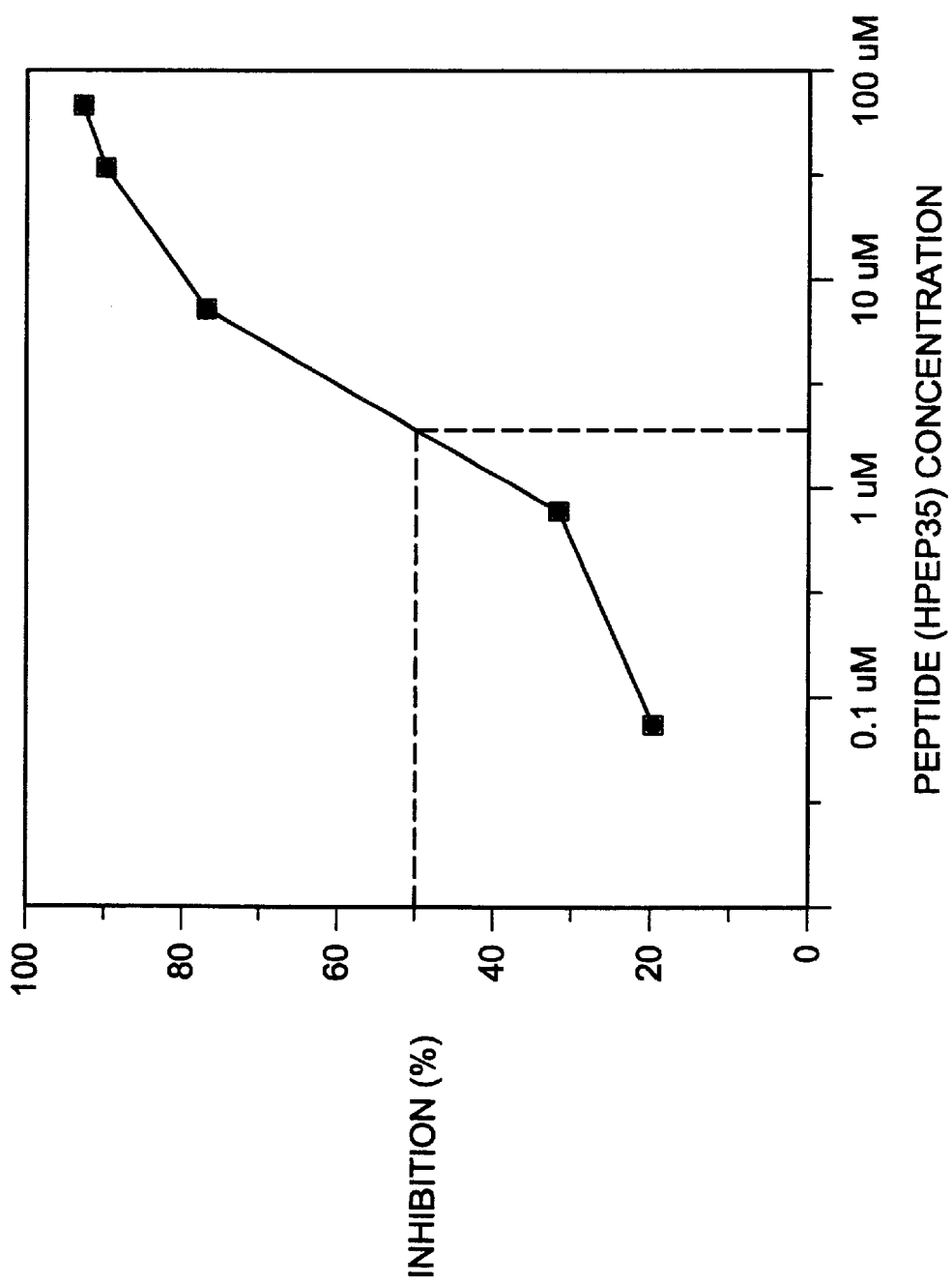
FIG. 2 is a graph showing that a peptide of the invention (HPEP35) inhibits erythrocyte binding to *P. vivax* Region II expressed by transfected Cos cells.

The present invention is directed to the binding site on the Duffy blood group antigen bound by Plasmodium Duffy-binding ligands. Sequence analysis of Duffy blood group proteins (gp-Fy) suggests that the human and rhesus Duffy antigens both contain nine putative transmembrane stretches, along with an approximately 66 amino acid, hydrophilic stretch at the N-terminus that is predicted to be extracellular (Chaudhuri et al. 1993; Chaudhuri et al. 1995). It has been found that a 35 amino acid peptide from the amino (NH$_2$) terminus of the human Duffy antigen serves as the binding site for both *P. vivax* and *P. knowlesi*. The same region of the corresponding Duffy antigen in the rhesus monkey is bound by the Duffy-binding of ligand *P. knowlesi*. It has also been found that glycosylation of the rhesus Duffy blood group antigen is involved in inhibiting the binding of the *P. vivax* Duffy-binding ligand to the rhesus Duffy antigen.

The invention further relates to a recombinantly produced gp-Fy protein containing the Fy$^a$ or the Fy$^b$ antigen, an allelic variation thereof, or a chimeric protein thereof. The present invention also relates to recombinantly produced unique fragments of a gp-Fy protein. Recombinant methods for producing proteins and fragments thereof are known in the art. Furthermore, the invention provides a synthetic gp-Fy protein, or a synthetic unique fragment thereof, again, produced in accordance with methods known in the art.

By "Duffy protein" is meant any mammalian gp-Fy protein which specifically binds a malarial Duffy-binding ligand. Accordingly, the term "Duffy protein" encompasses all naturally expressed Duffy blood group proteins having the specified binding affinity. Such naturally expressed Duffy proteins are found on the surfaces of red blood cells (and cells of other tissues) of mammals. Other functionally equivalent proteins having the specified binding affinity are also included within the scope of the invention. Thus, allelic forms of the gp-Fy proteins, as well as alternatively spliced products, are also included in the invention.

The invention also relates to Duffy-based proteins and characteristic fragments thereof expressed by eukaryotic and prokaryotic organisms and cells modified to express such proteins. Also, synthetically prepared proteins, including proteins having a sequence corresponding to a natural Duffy sequence or modified to incorporate alternative amino acid residues having little or no substantial detrimental effect on the specified binding of the malarial Duffy-binding ligand. The skilled artisan can use known methods to prepare a library of modified proteins to determine how the binding affinity of the protein for the malarial binding ligand is affected by specific amino acid substitution. Particularly preferred synthetic proteins are those which have a greater binding affinity for the malarial Duffy-binding ligand than a naturally expressed Duffy protein or fragment thereof A highly preferred Duffy protein according to the invention is a protein comprising the amino acid sequence AELSPSTENSSQLDFEDVWNSSYGVNDSFPDGDYD, designated herein SEQ ID NO:1. Proteins consisting of this sequence have been found to have significant and specific binding affinity for malarial Duffy-binding ligands. Based on the experimental information described in detail below, this sequence appears to define the binding site for the Duffy-binding ligand of malarial Plasmodia. The isolation of this sequence from the entire Duffy protein does not compromise the binding affinity of the sequence. Accordingly, it is to be expected that other proteins containing the specified sequence would have similar malarial-binding affinities. Such other proteins might otherwise differ substantially from naturally expressed Duffy protein, either in terms of the number of amino acid residues or in terms of the sequence of other residues.

The invention also includes malaria-inhibiting peptide fragments characteristic of the Plasmodium binding site of the Duffy protein of the rhesus monkey. In particular, a rhesus-based peptide corresponding to the HPEP35 peptide has been isolated which also interferes with binding between malarial Duffy-binding ligand and the human Duffy blood group antigen. This peptide, designated RHPEP34 has the sequence AELSPSTQNSSQLNSDLWNFSYDGNDSF-PDVDYD (SEQ ID NO:4). The amino acid differences between the human and rhesus Duffy antigens in the regions identified as the malarial binding sites are shown in FIG. 1A. Compared to the human Duffy antigen, eight amino acid substitutions and a single amino acid deletion are evident in the rhesus sequence in this region.

The invention, therefore, includes the RHPEP34 peptide, as well as peptides which include this peptide in their primary structure. That the degree of homology between the human and rhesus peptides is not complete implies that other substitutions and deletions (and possible additions) to the sequences will also have efficacy in inhibiting binding between the Duffy antigen and malarial Duffy-binding ligands. Accordingly, other Duffy-related peptides obtained from other species, which are at least substantially homologous to the human or rhesus peptides, and which exhibit the proper malarial inhibition, are also within the scope of the invention.

Other non-human primate Duffy proteins exhibit substantial homology with the human Duffy protein (Chaudhuri et al. 1995). In particular, chimpanzee (*Pan troglodytes*), aotus monkey (*Aotus trivirgatus*); and squirrel monkey (*Saimiri sciureus*) all are subject to infection by both *P. vivax* and *P. knowlesi*. The Duffy proteins from these species are most likely mediating these infections. Given what is now understood about the human malarial binding site of the human Duffy protein, peptides based on the Duffy proteins from these and other primate species are expected to inhibit infection of erythrocytes by Plasmodium organisms. Peptides comprising the malarial binding site of these primate Duffy proteins are, therefore, also within the scope of the invention. These peptides include, for example:

GELSPSTENSSQLNLEDLWDFSYDGNDSLPEIDY (SEQ ID NO:5) (characteristic of aotus monkey Duffy protein), and VELSPSTENSSQLNLEDLWNFSYNGNDSFPEIDY (SEQ ID NO:6) (characteristic of squirrel monkey Duffy protein).

The chimpanzee Duffy protein is exactly homologous to the human protein in the malarial binding region. Larger peptides including SEQ ID NO:5 or SEQ ID NO:6 are also contemplated as falling with the scope of the invention.

It has also been found that other fragments consisting of smaller portions of the HPEP35 peptide do not have significant binding affinity for malarial Duffy-binding ligands. Specifically, one peptide consisting of residues 1–13 of the HPEP35 peptide, and another peptide consisting of residues 14–35, have been studied. These peptides are designated HPEP13, having the sequence AELSPSTENSSQL (SEQ ID NO:7), and HPEP22, having the sequence DFEDVWNS-SYGVNDSFPDGDYD (SEQ ID NO:8). The relationships of each of these peptides to the HPEP35 peptide are shown in FIG. 1B. Both of these peptides have been found to have no significant binding affinity for the ligand.

Moreover, another peptide, designated HPEP3850 and having the sequence PSTENSSQLDFEDVWNSSYGVNDS (SEQ ID NO:9), consisting of residues 5–28 of the HPEP35 peptide, also does not bind to the malarial Duffy-binding ligand. (See FIG. 1B for the relationship of this peptide to the HPEP35 peptide.) This implies that the residues at positions 1–4 and 29–35 of HPEP35 are involved in the binding, either by direct interaction or by indirect e.g., steric, influence.

Surprisingly, the above observations are consistent with the relative binding affinities of each of these peptides for the Rubinstein anti-Fy6 antibody, which specifically binds the Duffy protein and certain fragments thereof In particular, the Rubinstein antibody binds to the HPEP35 peptide, but not to either of the HPEP13 or HPEP22 peptides. Previously, Rubinstein et al. hypothesized that the anti-Fy6 antibody might interfere with binding of the malarial Duffy-binding protein to expressed Duffy protein, but this conjecture was not proved. Prior to the present invention, no actual structural similarity between the malarial Duffy-binding ligand and the Rubinstein antibody had been established, and there had been no rational basis for expecting such highly similar binding affinities. Indeed, there had been no previous understanding of the domain in the Duffy protein involved in binding to the malarial ligands. Thus, that the Rubinstein antibody binding site and the malarial binding site actually coincide with such a high degree of functionality is fortuitous and unexpected.

Moreover, the Rubinstein peptide has been found to bind the following peptides in an ELISA assay:

MASSGYVLQAELSPSTENSSQLDFED-
VWNSSYGVNDSFPDGDYDANLEAAAPCH-
SCNLLDDSALPF (SEQ ID NO:2); and
MASSGYVLQAELSPSTENSSQLDFED-
VWNSSYGVNDSFPDGDYD (SEQ ID NO:10).

Each of these peptides contains the HPEP35 domain described above. Given the unusual correspondence between the binding of the HPEP35 peptide itself and each of the Rubinstein antibody and the malarial Duffy-binding ligand, there is now substantial reason to expect that the Duffy-binding ligand would bind these larger peptides as well. Thus, these peptides are within the scope of the invention.

In addition, the discovery of spliced and non-spliced mRNAs encoding two different naturally expressed Duffy proteins, designated gp-Fyα and gp-Fyβ. The differences have been found to obtain only in the N-terminal peptides of the two proteins. The Duffy protein which is encoded by the non-spliced mRNA (gp-Fyα) contains an N-terminus including the sequence $NH_2$-MASSGYVLQ (SEQ ID NO:11), while the spliced mRNA encodes a Duffy protein (gp-Fyβ) containing an N-terminus $NH_2$-MGNCLHR (SEQ ID NO:12). The two forms of the Duffy protein are identical thereafter. These two forms of Duffy protein are defined in U.S. application Ser. No. 08/749,543, filed on Nov. 15, 1996, the entire disclosure of which is incorporated by reference herein. It is reported there, that both forms of the gp-Fy protein bind the anti-Fy6 antibody. Because the N-terminal domains of the two forms of gp-Fy protein are distinct, it was originally thought that the Fy6 epitope could not be at that region of the protein. Surprising, however each of these forms of Duffy protein has affinity for the malarial binding ligand, implying that the differences between the two N-terminal differences are not significantly relevant to the malarial binding site. Proteins comprising the HPEP35 peptide and any or all of the N-terminal amino acid residues specified by the non-spliced or spliced mRNAs are, therefore, considered to be malarial-binding Duffy proteins according to the invention. Accordingly, such peptides include, for example:

MASSGYVLQAELSPSTENSSQLDFED-
VWNSSYGVNDSFPDGDYDANLEAAAPCH-
SCNLLDDSALPF (SEQ ID NO:2), and
MGNCLHRAELSPSTENSSQLDFEDVWNS-
SYGVNDSFPDGDYDANLEAAAPCHSCN-
LLDDSALPF (SEQ ID NO:3); along with fragments thereof containing the HPEP35 peptide, as well as peptides further comprising additional amino acids at their carboxy termini.

The invention includes functional equivalents of the peptides described herein. A peptide is considered a functional equivalent of the peptide of the invention if it functions to inhibit malarial binding or infection of Duffy-positive erythrocytes. The equivalent peptides will normally have substantially the same amino acid sequence as the peptide of the invention. However, an amino acid sequence that is substantially the same as another sequence, but that differs from the other sequence by means of one or more substitutions, additions and/or deletions is considered to be an equivalent sequence. Preferably, such substitutions, additions, or deletions constitute less than 25%, more preferably less than 10%, and most preferably less than 5% of the number of amino acid residues in the amino acid sequence of the peptide of the invention.

For example, it is possible to substitute amino acids in a sequence with equivalent amino acids. Groups of amino acids known normally to be equivalent are:

(a) Ala (A), Ser (S), Thr (T), Pro (P), Gly (G);
(b) Asn (N), Asp (D), Glu (E), Gln (Q);
(c) His (H), Arg (R), Lys (K);
(d) Met (M), Leu (L), Ile (I), Val (V); and
(e) Phe (F), Tyr (Y), Trp (W).

However, as is demonstrated by the cross-functionality of the human and rhesus peptides described above, substitutions outside these groups can be made without eliminating functional equivalence in the peptides according to the invention. Thus, substitutions, additions, and/or deletions in the peptides may be made as long as the resulting equivalent peptides have the same function as the peptides specifically described herein.

The peptides of the invention can be prepared from natural sources, i.e., by proteolytic cleavage of gp-Fy protein, or through chemical synthesis. Peptides corresponding to a portion of gp-Fy protein that contains the malarial binding site (receptor) also have been synthesized. Details on chemical synthesis of peptides and linkage of peptides to carriers can be found in U.S. Pat. Nos. 4,847,080 and 5,204,096. Such peptides have therapeutic usefulness comparable to that of gp-Fy protein itself and, as is the case with gp-Fy protein, the synthetic peptides can be combined with physiologically acceptable diluents to yield a composition effective against malarial infection, or a therapeutic agent useful to regulate essential erythrocyte, neural and renal functions.

gp-Fy protein and synthetic peptides corresponding to a portion of gp-Fy protein also have utility in the production of therapeutics or pharmaceuticals, e.g., antibodies, complementary peptides, and drugs modeled on the tertiary structure of the gp-Fy protein or synthetic peptides, which are also of therapeutic value in the treatment of malaria and in the regulation of essential erythrocyte, neural and renal functions.

In the antimalarial composition of the invention, the inhibitory peptide of the invention will usually be present along with a physiologically acceptable diluent (medium), e.g., phosphate buffered saline, optionally containing an adjuvant. Generally speaking, the amount of the peptide in the physiologically acceptable diluent will be between approximately 1 μg and 1 mg per dose. A suitable composition can be formulated using gp-Fy protein in similar amounts in similar diluents, although for most applications the use of synthetic peptides will be more practical.

In either case, the antimalarial composition of the invention can be administered by subcutaneous, intravenous, intradermal or intramuscular injection. While the preferred route would depend upon the particular composition, intramuscular injection will be generally suitable. Frequency of administration will vary depending on the composition as well as on the virulence of the particular strain of Plasmodium sought to be obstructed.

It is known, for example, from Adams J.H. (1992), that the binding regions identified in all malarial Plasmodium erythrocyte binding proteins are homologous. Therefore, gp-Fy protein and the peptides of the invention bind to and interfere with the erythrocyte binding of all Plasmodium species. This means that the peptides of the invention will be generally useful against all types of malaria and the invention, thus, extends to a method of protecting a warm-blooded animal against malaria due to any Plasmodium species, preferably, P. vivax and P. knowlesi.

The knowledge of the malaria-inhibiting peptides of the invention, together with the cloning and sequencing of the human and rhesus Duffy genes, enables other applications of the invention. For example, transgenic animals can be constructed using conventional transgenic techniques to express heterologous Duffy protein. Various such techniques are known, and certain of these techniques can yield heritability of the transgene. See, e.g., Pinkert et al. (1995) for an overview of these techniques, and the documents cited there for greater detail. A mammal can be transformed by integration of an expressible transgene comprising a heterologous Duffy-related nucleic acid sequence into the genome of the mammal. Preferably the transgene is heritable. Such a transgenic animal can then be used as an in vivo model for malarial infection in the species from which the Duffy gene is derived. Of particular importance, of course, is the development of animal models for human malarial infection. Such transgenic animal models would express a Duffy protein normally expressed in erythrocytes of humans, and would be capable of being bound by and infected by Plasmodium species capable of infecting humans, even if the normal host animal is not susceptible to those species.

In one exemplary approach a transgenic test animal is administered a putative antimalarial substance and inoculated using a malarial organism which would normally measurably bind erythrocytes and/or produce measurable infection in the modified animal. Following a time sufficient to produce a measurable effect in an otherwise untreated animal, binding to and/or infection of erythrocytes is measured. A lower than normal rate of binding or infection indicates that the putative antimalarial inhibits the organism's capacity for binding and/or infection in vivo.

Thus, variants of the peptide of the invention (or other unrelated substances) can be tested as prospective therapeutic antimalarials in these model animals, avoiding deliberate exposure of humans to the malarial organism. Other uses for such modified organisms will be evident to the skilled artisan.

Also, the peptides of the invention can be used, according to methods known in the art, as exquisitely precise immunogens for the development of monoclonal and polyclonal antibodies specific for the malarial binding site on a Duffy protein. For example, a peptide of the invention can be administered to a xenogenic animal, in which the peptide would be perceived as a non-self determinant. An immune response would be raised against the peptide, and polyclonal antibodies could be harvested.

Alternatively, a peptide of the invention is useful to prepare monoclonal antibodies having the same specificity as the Rubinstein antibody. The procedure for preparing such antibodies is essentially the same procedure employed by Rubinstein et al. except that instead of immunizing mice against human red cells, immunization is against gp-Fy peptide per se or a related peptide exhibiting similar immunogenicity.

Anti-idiotypic antibodies can also be made against one of these antibodies, using techniques known in the art. Such anti-idiotypic antibodies are expected to exhibit a capacity for specifically binding to the malarial parasite to prevent the parasite from binding to a Duffy-bearing erythrocyte.

The following examples are provided to assist in a further understanding of the invention. The particular materials and conditions employed are intended to be further illustrative of the invention and are not limiting upon the reasonable scope thereof.

EXAMPLE 1

A series of Duffy-based peptides was synthesized using an automated synthesizer as described by Parker et al. (1992). Amino acid compositional, mass spectrophotometric and analytical reversed-phase HPLC analyses were performed using conventional methods to confirm purity and sequence of the synthetic peptides. In some cases, protein sequence analysis was also performed to check the sequence of the peptides.

The following peptides, based on known sequences of human and rhesus Duffy proteins, were prepared:

HPEP35  AELSPSTENSSQLDFEDVWNSSYGVNDS-FPDGDYD (SEQ ID NO:1)

HPEP13 AELSPSTENSSQL (SEQ ID NO:7)

HPEP22 DFEDVWNSSYGVNDSFPDGDYD (SEQ ID NO:8)

HPEP3850 PSTENSSQLDFEDVWNSSYGVNDS (SEQ ID NO:9)

RHPEP34 AELSPSTQNSSQLNSDLWNFSYDGNDSF-PDVDYD (SEQ ID NO:4)

EXAMPLE 2

Region II, the 5' cysteine-rich region of the P. vivax Duffy antigen-binding protein (DABP) has previously been shown to possess adhesive, erythrocyte binding properties (Chitnis et al. 1994). Transfected Cos7 cells, expressing P. vivax Region II on the cell surface, bind Duffy-positive but not Duffy-negative human erythrocytes (Chitnis et al. 1994).

Plasmid constructs useful for expression of Region II of the P. vivax Duffy-binding protein (pHVDR22), the P. knowlesi Duffy-binding protein (pHKADR22), the P. knowlesi β protein (pHKBDR22) and P. falciparum EBA-175 (EBA-175 RII) on the Cos cell surface have been described previously (Chitnis et al. 1994; Sim et al. 1994). Each of these constructs contains DNA sequences encoding Region II of the parasite ligands fused with the signal sequence and transmembrane segment of Herpes simplex virus glycoprotein D (HSV gD). The fusion proteins are targeted to the Cos cell surface by the signal sequence of HSV gD, and are anchored to the surface by the transmembrane segment. These expression plasmids contain a SV40 origin of replication (SV40 ori), which allows replication in Cos7 cells, and a Rous sarcoma virus LTR (RSV LTR), which serves as a promoter for expression in Cos7 cells (Cohen et al. 1988).

Cos7 cells (American Type Culture Collection CRL 1651; Rockville, Md.) were cultured in Dulbecco's modified Eagle's medium (DMEM) with 10% heat inactivated fetal calf serum (both from GIBCO BRL, Gaithersburg, Md.) in a humidified $CO_2$ (5%) incubator at 37° C. Fresh monolayers of Cos7 cells were transfected in 3.5 cm diameter wells with 5 μg of plasmid DNA by the calcium phosphate precipitation method as described earlier (Chitnis et al. 1994). Cells were washed three times in phosphate buffered saline (PBS), 12–16 h after transfection.

Transfection efficiencies were determined by immunofluorescence assays at 48–60 h after transfection as described (Chitnis et al. 1994). Ascites fluid containing the monoclonal antibody DL6 (mAb DL6, kindly provided by Drs. Gary Cohen and Roselyn Eisenberg, University of Pennsylvania, Philadelphia, Pa.), which reacts against amino acids 272–279 of the mature HSV gD protein, was used as the primary antibody in immunofluorescence assays as described earlier (Cohen et al. 1988). Other suitable antibodies are commercially available.

EXAMPLE 3

To study the ability of peptides from the Duffy antigen to inhibit erythrocyte binding, a binding assay using the transfected Cos cells was employed, based on a method previously described (Chitnis et al. 1994). This method measures interaction between the malarial Duffy antigen binding ligand expressed by the Cos cells and Duffy protein on erythrocytes. The ability of an analyte to interfere with the cellular binding can be quantitated by comparing the number of Cos cells surrounded by rosettes of erythrocytes in the control versus the number of rosettes formed in the presence of the analyte.

Transfected Cos cells were preincubated for 1 h in a 5% $CO_2$ incubator at 37° C. in 0.9 mL of complete Dulbecco's modified Eagle's medium (cDMEM) containing a series of concentrations (0 to 100 $\mu$M) of the peptides. One hundred microliters of human or rhesus erythrocytes at a hematocrit of 10% were added to wells containing the peptides and allowed to bind over 2 h at 37° C. in a 5% $CO_2$ incubator. Non-adherent erythrocytes were removed by washing the Cos7 cells then with PBS. The numbers of rosettes were scored in 20 fields of view at a magnification of 40× using an inverted microscope. Inhibition curves were drawn for three independent experiments and used to determine concentrations of the peptides required to achieve 50% inhibition.

The peptides from the N-terminus of the human Duffy antigen were tested for their ability to inhibit binding of P. vivax Region II to human erythrocytes in the Cos cell binding assay. These representative peptides were chosen because the sequences occur in a domain recognized by Fy6, a monoclonal antibody to the human Duffy antigen (A. Chaudhuri, unpublished data) that can block erythrocyte invasion by P. vivax in vitro (Bamwell et al. 1989).

Table 1 summarizes data obtained in the Cos cell binding assay. Data are provided illustrating erythrocyte binding to transfected Cos cells expressing various malarial erythrocyte binding protein fragments, and comparing the inhibitory effects of the HPEPE35 and RHPEP34 peptides from the human and rhesus Duffy antigens. Average concentrations (± standard deviation) for the peptides HPEP35 and RHPEP34 at which 50% inhibition of binding is achieved are shown. Inhibition curves from three independent experiments were used to determine the average concentrations at which 50% inhibition is achieved. The highest concentration at which the peptides were tested was 100 $\mu$M. For those cases in which the inhibition was less than 5% at the highest peptide concentration used, i.e., 100 $\mu$M, the average concentrations for 50% inhibition is reported as ">100 $\mu$M." Numbers in the brackets show the number of independent experiments used for determination of the 50% inhibition concentrations.

TABLE 1

Inhibition of Erythrocyte Binding with Duffy Peptides

| Region II Source | Erythrocyte type | HPEP35 50% Inhibition Conc. ($\mu$m) | RHPEP34 50% Inhibition Conc. ($\mu$M) |
| --- | --- | --- | --- |
| P. vivax DABP | Human Fy(a+b+) | 2.9 ± 1.4 (3) | 2.1 ± 2.1 (3) |
| P. knowlesi-α | Human Fy(a+b+) | 4.1 ± 2.7 (3) | 5.5 ± 3.9 (3) |
| P knowlesi α | Rhesus | 13.1 ± 6.7 (3) | |
| P. knowlesi β | Rhesus | >100 (2) | >100 (2) |
| P. falciparum EBA-175 | Human Fy(a+b+) | >100 (2) | >100 (2) |

FIG. 2 shows an inhibition curve from one experiment in which HPEP35 was found to inhibit the binding of Duffy-positive erythrocytes to transfected Cos cells expressing P. vivax Region II. The concentration for 50% inhibition of erythrocyte binding was determined for each experiment from the inhibition curve as shown. HPEP35 was determined to inhibit the binding of Duffy-positive human erythrocytes to Cos cells expressing P. vivax Region II with 50% inhibition at a concentration of 2.9±1.4 $\mu$M (See Table 1, below).

The three smaller peptides from the 35 amino acid region of the human Duffy N-terminal domain (i.e., HPEP13, HPEP22 and HPEP3850) were also tested in the inhibition assays (data not shown). These three smaller peptides were found to have no effect on the binding of human erythrocytes to Region II of the P. vivax protein, even at concentrations up to 100 $\mu$M.

Table 1 also illustrates that HPEP35 inhibits the binding of human erythrocytes to Region II of the P. knowlesi Duffy antigen binding protein (α) with 50% inhibition at a concentration of 4.9±2.3 $\mu$M. It thus appears that the P. vivax and P. knowlesi ligands bind the same site on the human Duffy blood group antigen. Surprisingly, HPEP35 also inhibits the binding of rhesus erythrocytes to Region II of the P. knowlesi Duffy antigen binding protein (α) suggesting that the same site within the parasite domain is used for binding to both human and rhesus Duffy blood group antigens.

To rule out the possibility that the inhibition of binding observed with HPEP35 is a non-specific effect, we tested the ability of HPEP35 to inhibit the binding of erythrocytes to Region II of P. falciparum EBA-175 and Region II of the P. knowlesi β protein, neither of which binds the Duffy antigen. Region II of EBA-175 binds sialic acid residues of glycophorin A on human erythrocytes and Region II of the P. knowlesi β protein binds an as yet unidentified receptor on rhesus erythrocytes. HPEP35 had no effect on the binding of human erythrocytes to Region II of EBA-175 or the binding of rhesus erythrocytes to Region II of the P. knowlesi β protein at concentrations up to 100 $\mu$M (Table 1).

RHPEP34 was also found to inhibit binding of rhesus as well as human erythrocytes to Region II of the P. knowlesi Duffy-binding protein (Table 1). This implies that RHPEP34 indeed serves as the binding site on the rhesus Duffy antigen for the P. knowlesi ligand. As a test for specificity, we confirmed that RHPEP34 does not inhibit the binding of human erythrocytes to Region II of P. falciparum EBA-175 or the binding of rhesus erythrocytes to Region II of the P. knowlesi β protein, neither of which binds the Duffy antigen (Table 1).

We also tested the ability of RHPEP34 to inhibit the binding of human erythrocytes to Region II of the P. vivax Duffy antigen binding protein (Table 1). Since *P. vivax* Region II does not bind rhesus erythrocytes we expected that RHPEP34, a peptide from the rhesus Duffy antigen, would not inhibit the binding of human erythrocytes to *P. vivax* Region II. To our surprise, we found that RHPEP34 inhibits the binding of human Duffy positive erythrocytes to *P. vivax* Region II with 50% inhibition at concentrations of 2.1±2.1 μM (Table 1). It thus appears that, although *P. vivax* Region II does not bind the Duffy antigen on rhesus erythrocytes, *P. vivax* Region II can bind to a peptide from the rhesus Duffy antigen.

One possible reason for this anomalous result is that whereas the rhesus Duffy antigen is heavily glycosylated, the synthetic peptides used in the inhibition studies lack sugar residues. To determine if glycosylation of the rhesus Duffy blood group antigen influences binding, we studied the binding of normal and N-glycanase-treated rhesus erythrocytes to *P. vivax* Region II.

EXAMPLE 4

Blood was collected in 10% citrate/phosphate/dextrose (CPD) (Baxter, Deerfield, Ill.) and stored at 4° C. for up to four weeks. Standard blood banking methods using two antisera (anti-Fya and anti-Fyb) were used to determine the Duffy phenotypes. Duffy positive erythrocytes used in the binding assays had the Fy(a+b+) phenotype. Erythrocytes were washed three times in RPMI 1640 (GIBCO BRL) and resuspended to a hematocrit of 10% in RPMI 1640 for use in the erythrocyte binding assays. Washed human and rhesus erythrocytes were treated with neuraminidase as described earlier (Comus et al. 1985). Human and rhesus erythrocytes were deglycosylated with the N-glycanase, peptide-N-glycosidase F from *Flavobacterium meningosepticum* (Oxford Glycosystems). Washed erythrocytes (100 μL) were incubated with mixing for 1 h at 37° C. in 500 μL of PBS containing 10 units of N-glycanase and reaction buffer supplied by the manufacturer. The erythrocytes were washed extensively in PBS to remove the enzyme and stop the deglycosylation.

Table 2 illustrates the binding profile of *P. vivax* Region II. Transfected Cos cells expressing Region II of the *P. vivax* DABP were tested for binding to rhesus and human erythrocytes. Binding is reported as negative (−) when no rosettes were seen in the entire well. Where binding is reported a positive (+), approximately 100 to 200 rosettes were seen in 20 fields of view at 40× magnification. In each case immunofluorescence assays were performed to ensure that *P. vivax* Region II was expressed on the Cos cell surface. Transfection efficiencies were in the range of 2–5%.

TABLE 2

Binding Specificity of *P. vivax* DABP Region II

| Erythrocytes | Treatment | Binding |
| --- | --- | --- |
| Rhesus | None | − |
| Rhesus | N-Glycanase | + |
| Rhesus | Neuraminidase | − |
| Human Fy(a+b+) | None | + |
| Human Fy(a+b+) | N-glycanase | + |
| Human Fy(a−b−) | None | − |
| Human Fy(a−b−) | N-glycanase | − |

Whereas normal rhesus erythrocytes do not bind *P. vivax* Region II, N-glycanase-treated rhesus erythrocytes bind the *P. vivax* ligand (Table 2). This indicates that despite the differences in amino acid sequences, *P. vivax* can bind the peptide backbones of both the human and rhesus Duffy antigens. In retrospect, this surprising result helps to explain why RHPEP34, a peptide derived from the rhesus Duffy antigen inhibits the binding of human erythrocytes to *P. vivax* Region II.

EXAMPLE 5

We considered the possibility that enzymatic treatment with N-glycanase reduces the surface charge density on erythrocytes and leads to non-specific binding interactions. Another possibility that must be considered is that N-glycanase treatment may create a novel binding epitope independent of the Duffy blood group antigen. To test these possibilities, the following experiments were performed. Since sialic acids represent the most significant source of electric charge on the erythrocyte surface, neuraminidase-treated rhesus erythrocytes were tested for binding to *P. vivax* Region II. Neuraminidase-treated rhesus erythrocytes did not bind *P. vivax* Region II (Table 2). In the same experiment, neuraminidase-treated human erythrocytes did not bind Region II of EBA-175 indicating that the enzymatic removal of sialic acids was complete. Reduction of surface charge can not, therefore, account for the binding of N-glycanase-treated rhesus erythrocytes to *P. vivax* Region II. It was also found that N-glycanase-treated Duffy negative human erythrocytes do not bind *P. vivax* Region II (Table 2). This rules out the possibility that N-glycanase treatment may create a novel epitope that binds *P. vivax* Region II.

EXAMPLE 6

We have previously shown that the chemokine, melanoma growth stimulating activity (MGSA), binds the Duffy blood group antigen and can be used to inhibit the binding of *P. vivax* Region II to Duffy-positive human erythrocytes (Horuk et al. 1993; Chitnis et al. 1994).

To study the efficacy of the chemokine MGSA in inhibiting binding, erythrocytes were preincubated in media containing different concentrations of MGSA (0 to 1000 nM) for 1 h at room temperature before they were used in erythrocyte binding assays as described earlier (Su et al. 1995).

Table 3 summarizes data related to the efficacy of MGSA in inhibiting erythrocyte binding to transfected Cos cells expressing *P. vivax* Region II. Normal and N-glycanase-treated rhesus erythrocytes were preincubated with a series of concentrations (0, 0.1 nM, 1 nM, 10 nM, 100 nM, and 1000 nM) of MGSA, and used in binding assays with transfected Cos cells expressing *P. vivax* Region II. Table 3 reports data on the concentration of MGSA at which 50% inhibition of binding was achieved in separate experiments.

TABLE 3

Inhibition of Rhesus Erythrocyte Binding with MGSA

| Region II Source | Treatment | 50% Inhibition Conc. |
| --- | --- | --- |
| *P. knowlesi* α | None | 5 nM |
| *P. vivax* DABP | N-glycanase | 5 nM, 6 nM |
| P. knowlesi β | N-glycanase | >1 μM |

As shown in Table 3, MGSA was found to inhibit the binding of rhesus erythrocytes to Cos cells expressing Region II of the *P. knowlesi* Duffy-binding ligand (α).

To confirm that *P. vivax* Region II binds the peptide backbone of the deglycosylated rhesus Duffy blood group antigen, we tested if MGSA could inhibit the binding of N-glycanase-treated rhesus erythrocytes to *P. vivax* Region II. It was found that MGSA inhibits the binding of N-glycanase-treated rhesus erythrocytes to Region II of the *P. vivax* Duffy antigen binding protein, with 50% inhibition at nanomolar (nM) concentrations (Table 3). Inhibition of erythrocyte binding indicates that MGSA and *P. vivax* Region II bind the same molecule on N-glycanase-treated rhesus erythrocytes, namely the deglycosylated rhesus Duffy antigen. Glycosylation of the rhesus Duffy antigen thus appears to be involved in preventin the *P. vivax* Duffy-binding ligand from binding to rhesus erythrocytes. This may be the reason why rhesus erythrocytes are resistant to invasion by *P. vivax*. Glycosylation of the rhesus Duffy antigen may block binding to the *P. vivax* ligand by preventing access to the binding site on the peptide backbone or by altering the conformation of the binding site.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

BIBLIOGRAPHY

The following publications, mentioned in the foregoing specification, are incorporated herein by reference for all that they disclose:

Adams J. H., B. K. L. Sim, S. A. Dolan, X. Fang, D. C. Kaslow, and L. H. Miller, "A family of erythrocyte binding proteins of malaria parasites," *Proc. Natl. Acad. Sci. U.S.A.* 89:7085 (1992).

Barnwell J. W., M. E. Nichols, and P. Rubenstein, "In vitro evaluation of the role of the Duffy blood group in *Plasmodium vivax* erythrocyte invasion," *J. Exp. Med.* 169:162 (1989).

Baruch D. I., B. L. Pasloske, H. B. Singh, B. Xiabui, X. C. Ma, M. Feldman, T. F. Taraschi, and R. J. Howard, "Cloning the *Plasmodium falciparum* gene encoding PfEMP-1, a malarial variant antigen and adherence receptor on the surface of parasitized human erythrocytes," *Cell* 82:77 (1995).

Camus D. and T. J. Hadley, "A *Plasmodium falciparum* antigen binds to host erythrocytes and merozoites," *Science* 187:748 (1985).

Chaudhuri A., J. Polyakova, V. Zbrzezna, and A. O. Pogo, "The coding sequence of Duffy blood group gene in humans and simians: Restriction fragment length polymorphism, antibody and malarial parasite specificities, and expression in nonerythroid tissues in Duffy-negative individuals," *Blood* 85(3):615–621 (1995).

Chaudhuri A., J. Polyakova, V. Zbrzezna, K. Williams, S. Gulati, and A. O. Pogo, "Cloning of glycoprotein D cDNA, which encodes the major subunit of the Duffy blood group system and the receptor for the *Plasmodium vivax* malaria parasite," *Proc. Natl. Acad. Sci. USA* 90:10793 (1993).

Chitnis C. E. and L. H. Miller, "Identification of the erythrocyte binding domains of *Plasmodium vivax* and *Plasmodium knowlesi* proteins involved in erythrocyte invasion," *J. Exp. Med.* 180:497 (1994).

Cohen G. H., W. C. Wilcox, D. L. Sodora, D. Long, J. Z. Levin, and R. J. Eisenberg, "Expression of Herpes simplex virus type 1 glycoprotein D gene: nucleotide sequence and expression in *Escherichia coli*," *J. Virol.* 62:1932 (1988).

Dolan S. A., J. L. Proctor, D. W. Alling, Y. Okubo, T. E. Wellems, and L. H. Miller, "Glycophorin B as an EBA-175 independent *Plasmodium falciparum* receptor of human erythrocytes," (1994).

Hadley T. J., F. W. Klotz, G. Pasvol, J. D. Haynes, M. H. McGinnis, Y. Okubo, and L. H. Miller, "Falciparum malaria parasites invade erythrocytes that lack glycophorin A and B (MkMk)," 1987. *J. Clin. Invest.* 80:1190 (1986).

Haynes D. J., J. P. Dalton, F. W. Klotz, M. H. McGinnis, T. J. Hadley, D. E. Hudson, and L. H. Miller, "Receptor-like specificity of a *Plasmodium knowlesi* malarial protein that binds to Duffy antigen ligands on erythrocytes," *J. Exp. Med.* 167:1873 (1988).

Hommel M., "Antigen variation in malaria parasites," *Immunol. Today* 6:28 (1985).

Horuk R. C., E. Chitnis, W. C. Darbonne, T. J. Colby, A Rybicki, T. J. Hadley, and L. H. Miller, "A receptor for the malaria parasite *Plasmodium vivax*: the erythrocyte chemokine receptor," *Science* 261:1182 (1993).

Livingston F. B., "The Duffy blood groups, vivax malaria and malaria sections in human populations: Review," *Human Biol.* 56:413 (1984).

Marsh W. L., "Present status of the Duffy blood group system," *Crit. Rev. Clin. Lab. Sci.* 5:387 (1975).

Miller L. H., S. J. Mason, D. F. Clyde, and M. H. McGinnis, "The resistance factor to *Plasmodium vivax* in Blacks: Duffy blood group genotype, FyFy," *N. Engl. J. Med.* 295:302 (1976).

Miller L. H., S. J. Mason, J. A. Dvorak, M. H. McGinnis, and I. K. Rothman, "Erythrocyte receptors for (*Plasmodium knowlesi*) malaria: Duffy blood group determinants," *Science* 189:561 (1975).

Mitchell G. H., T. J. Hadley, M. H. McGinnis, F. W. Klotz, and L. H. Miller, "Invasion of erythrocytes by *Plasmodium falciparum* malaria parasites: evidence for a receptor heterogeneity and two receptors," *Blood* 67:1519 (1986).

Nichols M. E., P. Rubinstein, J. D. Barnwell, S. R. de Cordoba, and R. E. Rosenfield, "A new human Duffy blood group specificity defined by a murine monoclonal antibody," *J. Exp. Med.* 166:776 (1987).

Parker K. C., B. M. Carreno, L. Sestak, U. Utz, W. E. Biddison, and J. E. Colligan, "Peptide binding to HLA-A2 and HLA-B27 isolated from *Escherichia coli*," *J. Biol Chem.* 267:5451 (1992).

Perkins M. E. and E. A. Holt, "Erythrocyte receptor recognition varies in *Plasmodium falciparum* isolates," *Mol. Biochem. Parasitol.* 27:23 (1988).

Pinkert C. A., M. H. Irwin, and R. J. Moffatt, "Transgenic animal modeling," pp. 901–907 in *Molecular Biology and Biotechnology: A Comprehensive Desk Reference*, R. A. Myers, ed., VCH Publishers, Inc., New York (1995).

Sim B. K. L., C. E. Chitnis, K. Wasniowska, T. J. Hadley, and L. H. Miller, "Receptor and ligand domains for *Plasmodium falciparum* malaria invasion of erythrocytes," *Science* 264:1941 (1994).

Smith J. D., C. E. Chitnis, A. G. Craig, D. J. Roberts, D. E. Hudson-Taylor, D. S. Peterson, R. Pinches, C. I. Newbold, and L. H. Miller, "Switches in expression of *Plasmodium falciparum* var genes correlate with changes in antigenic and cytoadherent phenotypes of infected erythrocytes," *Cell* 82:101 (1995). Su X. Z., V. Heatwole, S. P. Wetheimer, F. Guinet, J. A. Herrfeldt, D. S. Peterson, J. A. Ravetch, and T. E. Wellems, "The large diverse gene family var encodes proteins involved in cytoadherence and antigenic variation of *Plasmodium falciparum*-infected erythrocytes," *Cell* 82:89 (1995).

Zavala F., A. Masuda, P. M. Graves, V. Nussenzweig, and R. Nussenweig, "Ubiquity of the repetitive epitope of the CS protein in different isolates of human malaria parasites," *J. Immunol.* 135:2790 (1985).

What is claimed is:

1. A peptide consisting of an incomplete continuous fragment of a Duffy protein comprising a malarial binding site on
   AELSPSTENSSQLDFEDVWNSSYGVNDSFPDGDYD (SEQ ID NO:1) or comprising an amino acid sequence substantially homologous to
   AELSPSTENSSQLDFEDVWNSSYGVNDSFPDGDYD (SEQ ID NO:1) wherein said fragment inhibits the binding of Plasmodium species to a Duffy antigen on a mammalian cell.

2. A peptide according to claim 1, wherein said amino acid sequence substantially homologous to
   AELSPSTENSSQLDFEDVWNSSYGVNDSFPDGDYD (SEQ ID NO:1) comprises:
   MASSGYVLQAELSPSTENSSQLDFED-VWNSSYGVNDSFPDGDYDANLEAAAPCH-SCNLLDDSALPF (SEQ ID NO:2) or
   MGNCLHRAELSPSTENSSQLDFEDVWNS-SYGVNDSFPDGDYDANLEAAAPCHSCN-LLDDSALPF (SEQ ID NO:3) or
   AELSPSTQNSSQLNSDLWNFSYDGNDSF-PDVDYD (SEQ ID NO:4) or
   GELSPSTENSSQLNLEDLWDFSYDGND-SLPEIDYD (SEQ ID NO:5) or
   VELSPSTENSSQLNLEDLWNFSYNGNDS-FPEIDYD (SEQ ID NO:6).

3. A peptide according to claim 1, wherein said malarial binding site is on an erythrocyte surface protein of a non-human primate.

4. A peptide according to claim 1, wherein said malarial binding site is specifically bound by Rubinstein antibody.

5. A peptide according to claim 1 wherein said Plasmodium species is *Plasmodium vivax* or *Plasmodium knowlesi*.

6. A composition useful to protect a warm-blooded animal against infection by Plasmodium species, comprising an amount effective therefor of a peptide consisting of an incomplete continuous fragment of a Duffy protein comprising a malarial binding site on
   AELSPSTENSSQLDFEDVWNSSYGVNDSFPDGDYD (SEQ ID NO:1) or comprising an amino acid sequence substantially homologous to
   AELSPSTENSSQLDFEDVWNSSYGVNDSFPDGDYD (SEQ ID NO:1) wherein said fragment inhibits the binding of Plasmodium species to a Duffy antigen on a mammalian cell, said peptide in admixture with a physiologically acceptable diluent.

7. A composition according to claim 6, wherein said peptide is conjugated to a carrier.

8. A composition according to claim 6, wherein said Plasmodium species is *Plasmodium vivax* or *Plasmodium knowlesi* and said peptide inhibits binding of *Plasmodium vivax* or *Plasmodium knowlesi* to a red blood cell.

9. A composition according to claim 6, wherein said malarial binding site is specifically bound by Rubinstein antibody.

10. A composition useful to protect a warm-blooded animal against infection by Plasmodium species, according to claim 6, wherein said amino acid sequence substantially homologous to
    AELSPSTENSSQLDFEDVWNSSYGVNDSFPDGDYD (SEQ ID NO:1) comprises:
    MASSGYVLQAELSPSTENSSQLDFED-VWNSSYGVNDSFPDGDYDANLEAAAPCH-SCNLLDDSALPF (SEQ ID NO:2) or
    MGNCLHRAELSPSTENSSQLDFEDVWNS-SYGVNDSFPDGDYDANLEAAAPCHSCN-LLDDSALPF (SEQ ID NO:3) or
    AELSPSTQNSSQLNSDLWNFSYDGNDSF-PDVDYD (SEQ ID NO:4) or
    GELSPSTENSSQLNLEDLWDFSYDGND-SLPEIDYD (SEQ ID NO:5) or
    VELSPSTENSSQLNLEDLWNFSYNGNDS-FPEIDYD (SEQ ID NO:6).

11. A composition according to claim 10, wherein said Plasmodium species is *Plasmodium vivax* or *Plasmodium knowlesi*.

12. A method of protecting a warm-blooded animal from malarial infection by Plasmodium species, comprising administering to said animal an effective amount therefor of a peptide consisting of an incomplete continuous fragment of a Duffy protein comprising a malarial binding sire on
    AELSPSTENSSQLDFEDVWNSSYGVNDSFPDGDYD (SEQ ID NO:1) or comprising an amino acid sequence substantially homologous to
    AELSPSTENSSQLDFEDVWNSSYGVNDSFPDGDYD (SEQ ID NO:1) wherein said fragment inhibits the binding of Plasmodium species to a Duffy antigen on a mammalian cell.

13. A method according to claim 12, wherein said Plasmodium species is *Plasmodium vivax* or *Plasmodium knowlesi*.

14. A method according to claim 13, wherein said peptide inhibits binding of *Plasmodium vivax* or *Plasmodium knowlesi* to a red blood cell.

15. A method according to claim 14, wherein said amino acid sequence substantially homologous to
    AELSPSTENSSQLDFEDVWNSSYGVNDSFPDGDYD (SEQ ID NO: 1) comprises:
    MASSGYVLQAELSPSTENSSQLDFED-VWNSSYGVNDSFPDGDYDANLEAAAPCH-SCNLLDDSALPF (SEQ ID NO:2) or
    MGNCLHRAELSPSTENSSQLDFEDVWNS-SYGVNDSFPDGDYDANLEAAAPCHSCN-LLDDSALPF (SEQ ID NO:3) or
    AELSPSTQNSSQLNSDLWNFSYDGNDSF-PDVDYD (SEQ ID NO:4) or
    GELSPSTENSSQLNLEDLWDFSYDGND-SLPEIDYD (SEQ ID NO:5) or
    VELSPSTENSSQLNLEDLWNFSYNGNDS-FPEIDYD (SEQ ID NO:6).

16. A method according to claim 12, wherein said malarial binding site is specifically bound by Rubinstein antibody.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
          (A) LENGTH: 35 amino acids
          (B) TYPE: amino acid
          (D) TOPOLOGY: linear (ii) MOLECULE TYPE: peptide (iii) SEQUENCE DESCRIPTION: SEQ ID NO:1:

Ala Glu Leu Ser Pro Ser Thr Glu Asn Ser Ser Gln Leu Asp Phe
1               5                  10                  15

Glu Asp Val Trp Asn Ser Ser Tyr Gly Val Asn Asp Ser Phe Pro
                20                  25                  30

Asp Gly Asp Tyr Asp
                35

(2) INFORMATION FOR SEQ ID NO:2:

(i) SEQUENCE CHARACTERISTICS:
          (A) LENGTH: 66 amino acids
          (B) TYPE: amino acid
          (D) TOPOLOGY: linear (ii) MOLECULE TYPE: peptide (iii) SEQUENCE DESCRIPTION: SEQ ID NO:2:

Met Ala Ser Ser Gly Tyr Val Leu Gln Ala Glu Leu Ser Pro Ser
1               5                  10                  15

Thr Glu Asn Ser Ser Gln Leu Asp Phe Glu Asp Val Trp Asn Ser
                20                  25                  30

Ser Tyr Gly Val Asn Asp Ser Phe Pro Asp Gly Asp Tyr Asp Ala
                35                  40                  45

Asn Leu Glu Ala Ala Ala Pro Cys His Ser Cys Asn Leu Leu Asp
                50                  55                  60

Asp Ser Ala Leu Pro Phe
                65

(2) INFORMATION FOR SEQ ID NO:3:

(i) SEQUENCE CHARACTERISTICS:
          (A) LENGTH: 64 amino acids
          (B) TYPE: amino acid
          (D) TOPOLOGY: linear (ii) MOLECULE TYPE: peptide (iii) SEQUENCE DESCRIPTION: SEQ ID NO:3:

Met Gly Asn Cys Leu His Arg Ala Glu Leu Ser Pro Ser Thr Glu
1               5                  10                  15

Asn Ser Ser Gln Leu Asp Phe Glu Asp Val Trp Asn Ser Ser Tyr
                20                  25                  30

Gly Val Asn Asp Ser Phe Pro Asp Gly Asp Tyr Asp Ala Asn Leu
                35                  40                  45

Glu Ala Ala Ala Pro Cys His Ser Cys Asn Leu Leu Asp Asp Ser
                50                  55                  60

Ala Leu Pro Phe (2) INFORMATION FOR SEQ ID NO:4:

(i) SEQUENCE CHARACTERISTICS:
        (A) LENGTH: 34 amino acids
        (B) TYPE: amino acid
        (D) TOPOLOGY: linear (ii) MOLECULE TYPE: peptide (iii) SEQUENCE DESCRIPTION: SEQ ID NO:4:

```
Ala Glu Leu Ser Pro Ser Thr Gln Asn Ser Ser Gln Leu Asn Ser
1               5                  10                  15

Asp Leu Trp Asn Phe Ser Tyr Asp Gly Asn Asp Ser Phe Pro Asp
                20                  25                  30

Val Asp Tyr Asp
```

(2) INFORMATION FOR SEQ ID NO:5:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (iii) SEQUENCE DESCRIPTION: SEQ ID NO:5:

```
Gly Glu Leu Ser Pro Ser Thr Glu Asn Ser Ser Gln Leu Asn Leu
1               5                  10                  15

Glu Asp Leu Trp Asp Phe Ser Tyr Asp Gly Asn Asp Ser Leu Pro
                20                  25                  30

Glu Ile Asp Tyr Asp
                35
```

(2) INFORMATION FOR SEQ ID NO:6:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (iii) SEQUENCE DESCRIPTION: SEQ ID NO:6:

```
Val Glu Leu Ser Pro Ser Thr Glu Asn Ser Ser Gln Leu Asn Leu
1               5                  10                  15

Glu Asp Leu Trp Asn Phe Ser Tyr Asn Gly Asn Asp Ser Phe Pro
                20                  25                  30

Glu Ile Asp Tyr Asp
                35
```

(2) INFORMATION FOR SEQ ID NO:7:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (iii) SEQUENCE DESCRIPTION: SEQ ID NO:7:

```
Ala Glu Leu Ser Pro Ser Thr Glu Asn Ser Ser Gln Leu
1               5                  10
```

(2) INFORMATION FOR SEQ ID NO:8:

(i) SEQUENCE CHARACTERISTICS:
    (A) LENGTH: 22 amino acids
    (B) TYPE: amino acid
    (D) TOPOLOGY: linear (ii) MOLECULE TYPE: peptide (iii) SEQUENCE DESCRIPTION: SEQ ID NO:8:

Asp Phe Glu Asp Val Trp Asn Ser Ser Tyr Gly Val Asn Asp Ser
1               5                   10                  15

Phe Pro Asp Gly Asp Tyr Asp
                20

(2) INFORMATION FOR SEQ ID NO:9:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (iii) SEQUENCE DESCRIPTION: SEQ ID NO:9:

Pro Ser Thr Glu Asn Ser Ser Gln Leu Asp Phe Glu Asp Val Trp
1               5                   10                  15

Asn Ser Ser Tyr Gly Val Asn Asp Ser
                20

(2) INFORMATION FOR SEQ ID NO:10:

(i) SEQUENCE CHARACTERISTICS:
        (A) LENGTH: 44 amino acids
        (B) TYPE: amino acid
        (D) TOPOLOGY: linear (ii) MOLECULE TYPE: peptide (iii) SEQUENCE DESCRIPTION: SEQ ID NO:10:

Met Ala Ser Ser Gly Tyr Val Leu Gln Ala Glu Leu Ser Pro Ser
1               5                   10                  15

Thr Glu Asn Ser Ser Gln Leu Asp Phe Glu Asp Val Trp Asn Ser
                20                  25                  30

Ser Tyr Gly Val Asn Asp Ser Phe Pro Asp Gly Asp Tyr Asp
                35                  40

(2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (iii) SEQUENCE DESCRIPTION: SEQ ID NO:11:

Met Ala Ser Ser Gly Tyr Val Leu Gln
1               5

(2) INFORMATION FOR SEQ ID NO:12:

(i) SEQUENCE CHARACTERISTICS:
        (A) LENGTH: 7 amino acids
        (B) TYPE: amino acid
        (D) TOPOLOGY: linear (ii) MOLECULE TYPE: peptide -continued (iii) SEQUENCE DESCRIPTION: SEQ ID NO:12:

Met Gly Asn Cys Leu His Arg
1               5